US009616171B2

(12) United States Patent
Qin et al.

(10) Patent No.: US 9,616,171 B2
(45) Date of Patent: Apr. 11, 2017

(54) CONFORMABLE PATCH PUMP

(71) Applicant: Cam Med LLC, West Newton, MA (US)

(72) Inventors: Yanzhe Qin, Cambridge, MA (US); Zhifei Ge, Cambridge, MA (US)

(73) Assignee: Cam Med LLC, West Newton, MA (US)

( * ) Notice: Subject to any disclaimer, the term of this patent is extended or adjusted under 35 U.S.C. 154(b) by 0 days.

(21) Appl. No.: 15/015,627

(22) Filed: Feb. 4, 2016

(65) Prior Publication Data

US 2016/0193407 A1 Jul. 7, 2016

Related U.S. Application Data

(63) Continuation of application No. PCT/US2014/049755, filed on Aug. 5, 2014.
(Continued)

(51) Int. Cl.
*A61M 31/00* (2006.01)
*A61M 5/168* (2006.01)
(Continued)

(52) U.S. Cl.
CPC .... *A61M 5/16881* (2013.01); *A61M 5/14248* (2013.01); *A61M 5/14586* (2013.01);
(Continued)

(58) Field of Classification Search
CPC ................ A61M 5/14248; A61M 2005/14252
(Continued)

(56) References Cited

U.S. PATENT DOCUMENTS 3,921,636 A 11/1975 Zaffaroni
4,282,872 A 8/1981 Franetzki et al.
(Continued)

FOREIGN PATENT DOCUMENTS

EP 2657699 A1 10/2013
JP 2005351882 A 12/2005
(Continued)

OTHER PUBLICATIONS

Sven Spieth, et al., "An intra-cerebral drug delivery system for freely moving animals", Biomedical Microdevices, Klewer Academic publishers Bo., Vo. 14, No. 5, (May 24, 2012); pp. 799-809.
(Continued)

*Primary Examiner* — Edelmira Bosques
(74) *Attorney, Agent, or Firm* — Goodwin Procter LLP

(57) ABSTRACT

A flexible patch pump for controllable accurate subcutaneous delivery of one or more medicaments to a patient includes a laminated layered structure. The pump may have a rigid reservoir layer including a number of rigid reservoirs disposed in a flexible material; a flexible microfluidic layer including a compliant membrane for sealing the rigid reservoirs, a network of microfluidic channels connecting the rigid reservoirs, and a number of inlet and/or outlet valves corresponding to the rigid reservoirs; and a flexible-rigid electronic circuit layer including a number of individually-addressable actuators. In operation, the rigid reservoirs may contain medicament that is dispensed in precise volumes at appropriate times due, for example, to a pressure change in an addressed reservoir caused by displacement of the compliant membrane or other actuation element.

29 Claims, 16 Drawing Sheets

Related U.S. Application Data

(60) Provisional application No. 62/007,770, filed on Jun. 4, 2014, provisional application No. 61/862,124, filed on Aug. 5, 2013.

(51) Int. Cl.

| | | |
|---|---|---|
| *A61M 5/145* | (2006.01) | |
| *F04B 43/04* | (2006.01) | |
| *A61M 5/142* | (2006.01) | |
| *B81C 1/00* | (2006.01) | |
| *A61M 39/24* | (2006.01) | |
| *F04B 53/10* | (2006.01) | |
| *F16K 99/00* | (2006.01) | |

(52) U.S. Cl.
CPC ......... *A61M 39/24* (2013.01); *B81C 1/00158* (2013.01); *F04B 43/043* (2013.01); *F04B 53/10* (2013.01); *A61M 2005/14252* (2013.01); *A61M 2205/3334* (2013.01); *A61M 2205/35* (2013.01); *A61M 2205/581* (2013.01); *A61M 2205/582* (2013.01); *A61M 2207/00* (2013.01); *B81B 2201/036* (2013.01); *B81C 2201/034* (2013.01); *F16K 2099/008* (2013.01); *F16K 2099/0094* (2013.01)

(58) Field of Classification Search
USPC ....................................................... 604/506
See application file for complete search history.

(56) References Cited

U.S. PATENT DOCUMENTS

| | | | |
|---|---|---|---|
| 4,585,652 A | 4/1986 | Miller et al. | |
| 4,731,051 A | 3/1988 | Fischell | |
| 4,883,457 A | 11/1989 | Sibalis | |
| 5,053,001 A | 10/1991 | Reller et al. | |
| 5,167,625 A | 12/1992 | Jacobsen et al. | |
| 5,290,240 A * | 3/1994 | Horres, Jr. ............ | A61M 5/145 128/DIG. 12 |
| 5,474,527 A | 12/1995 | Bettinger | |
| 5,522,798 A | 6/1996 | Johnson et al. | |
| 5,527,288 A | 6/1996 | Gross et al. | |
| 5,575,770 A | 11/1996 | Melsky et al. | |
| 6,485,462 B1 | 11/2002 | Kriesel | |
| 6,656,159 B2 | 12/2003 | Flaherty | |
| 6,730,072 B2 * | 5/2004 | Shawgo ................ | A61B 5/145 128/898 |
| 6,749,587 B2 | 6/2004 | Flaherty | |
| 6,855,133 B2 | 2/2005 | Svedman | |
| 6,939,324 B2 | 9/2005 | Gonnelli et al. | |
| 7,070,592 B2 | 7/2006 | Santini, Jr. et al. | |
| 7,162,297 B2 | 1/2007 | Rossi | |
| 7,231,839 B2 | 6/2007 | Huber et al. | |
| 7,368,190 B2 | 5/2008 | Heller et al. | |
| 7,392,080 B2 | 6/2008 | Eppstein et al. | |
| 7,399,401 B2 | 7/2008 | Rush | |
| 7,455,667 B2 | 11/2008 | Uhland et al. | |
| 7,473,248 B2 | 1/2009 | Santini, Jr. et al. | |
| 7,510,551 B2 | 3/2009 | Uhland et al. | |
| 7,910,151 B2 | 3/2011 | Uhland et al. | |
| 8,095,197 B2 | 1/2012 | Santini, Jr. et al. | |
| 8,197,844 B2 | 6/2012 | Yanaki | |
| 8,211,092 B2 | 7/2012 | Uhland et al. | |
| 8,285,328 B2 | 10/2012 | Caffey et al. | |
| 8,343,092 B2 | 1/2013 | Rush et al. | |
| 8,551,044 B2 | 10/2013 | Burke et al. | |
| 8,591,498 B2 | 11/2013 | John | |
| 2002/0022798 A1 | 2/2002 | Connelly et al. | |
| 2002/0107470 A1* | 8/2002 | Richards ............ | A61K 9/0009 604/20 |
| 2003/0014014 A1* | 1/2003 | Nitzan ............ | A61M 5/14216 604/158 |
| 2003/0069560 A1* | 4/2003 | Adamis ................ | A61F 9/0017 604/521 |
| 2004/0064096 A1 | 4/2004 | Flaherty et al. | |
| 2004/0112529 A1* | 6/2004 | Karlsson ............ | B01J 19/0093 156/306.6 |
| 2004/0112989 A1 | 6/2004 | Poutiatine | |
| 2004/0121486 A1 | 6/2004 | Uhland et al. | |
| 2005/0016558 A1 | 1/2005 | Krogt | |
| 2005/0065466 A1 | 3/2005 | Vedrine | |
| 2007/0219496 A1 | 9/2007 | Kamen et al. | |
| 2008/0008845 A1 | 1/2008 | Oh et al. | |
| 2009/0155326 A1 | 6/2009 | Mack et al. | |
| 2010/0196445 A1 | 8/2010 | David et al. | |
| 2011/0054285 A1 | 3/2011 | Searle et al. | |
| 2011/0060280 A1 | 3/2011 | Caffey et al. | |
| 2011/0264028 A1 | 10/2011 | Ramdas et al. | |
| 2011/0313357 A1 | 12/2011 | Skutnik et al. | |
| 2011/0319861 A1 | 12/2011 | Wilk | |
| 2012/0116314 A1 | 5/2012 | Sexton | |
| 2012/0226265 A1 | 9/2012 | Chiao et al. | |
| 2013/0324949 A1 | 12/2013 | Kliman | |

FOREIGN PATENT DOCUMENTS

| | | |
|---|---|---|
| JP | 2006348906 A | 12/2006 |
| JP | 2010085333 A | 4/2010 |
| WO | WO-9202211 A1 | 2/1992 |
| WO | WO-9417853 A1 | 8/1994 |
| WO | WO-9426348 A1 | 11/1994 |
| WO | WO-2004026281 A2 | 4/2004 |
| WO | WO-2004093818 A2 | 11/2004 |
| WO | WO-2005058385 A2 | 6/2005 |
| WO | WO-2006015299 A2 | 2/2006 |
| WO | WO-2006124584 A2 | 11/2006 |
| WO | WO-2006127905 A2 | 11/2006 |
| WO | WO-2006133103 A2 | 12/2006 |
| WO | WO-2007129317 A1 | 11/2007 |
| WO | WO-2008051924 A2 | 5/2008 |
| WO | WO-2009109344 A1 | 9/2009 |
| WO | WO-2010038182 A2 | 4/2010 |
| WO | WO-2010100213 A1 | 9/2010 |
| WO | WO-2011022484 A1 | 2/2011 |
| WO | WO-2011139486 A2 | 11/2011 |
| WO | WO-2012072555 A1 | 6/2012 |
| WO | WO-2013032841 A1 | 3/2013 |
| WO | WO-2013075109 A2 | 5/2013 |
| WO | WO-2013097955 A1 | 7/2013 |
| WO | WO-2013106155 A1 | 7/2013 |
| WO | WO-2013119843 A1 | 8/2013 |
| WO | WO-2013134634 A1 | 9/2013 |
| WO | WO-2013158431 A1 | 10/2013 |
| WO | WO-2014036112 A1 | 3/2014 |

OTHER PUBLICATIONS

International Search Report and Written Opinion for PCT/US2014/049755, mailed Nov. 3, 2014.

Noo Li Jeon, et al. "Design and Fabrication of Integrated Passive Valves and Pumps for Flexible Polymer 3-Dimensional Microfluidic Systems", Biomedical Microdevices, 4:2, 117-121, 2002.

Ayumi Kabata, et al. "Prototype Micropump for Insulin Administration Based on Electrochemical Bubble Formation", Journal of Pharmaceutical Sciences, vol. 97, No. 11, Nov. 2008 pp. 5037-5045.

* cited by examiner

2302

CONFORMABLE PATCH PUMP

CROSS REFERENCE TO RELATED APPLICATIONS

This application is a continuation of and claims priority to International Patent Application No. PCT/US2014/049755, titled "Conformable Patch Pump," filed on Aug. 5, 2014, which claims priority to U.S. provisional patent application Ser. No. 62/007,770, titled "Conformable Patch Pump," filed on Jun. 4, 2014, and U.S. provisional patent application Ser. No. 61/862,124, titled "Flexible Thin Infusion Pump With Self-Regulation Reservoir Arrays," filed on Aug. 5, 2013, the disclosures of all three of which are herein incorporated by reference in their entireties.

TECHNICAL FIELD

In general, various embodiments of this invention relate to flexible patch pumps for use in delivering medicament to a patient and, specifically, to a patch pump including a plurality of rigid reservoirs disposed in a flexible material capable of accurately delivering precise amounts of medicament.

BACKGROUND

The treatment of many medical conditions requires the subcutaneous delivery of a medicament. As one example, the treatment of diabetes requires the subcutaneous delivery of insulin. In some instances, subcutaneously delivered medicament must be continuously delivered in small and at time varying doses over along period of time. It is important that such delivery be accurate, as over or under delivery can cause serious health risks. For example, the subcutaneous delivery of insulin can require accuracies as low as 0.5 microliters per hour. One widely used technique for subcutaneously delivering medicament is by pumping the medicament from a large external storage container through a long tube to a cannula of an infusion set attached to a patient's skin. An improvement over this technique is the use of a patch pump. A patch pump incorporates the medicament, pumping mechanism, and infusion set into a patch that attaches to a patient's skin, thus eliminating the need for long tubes. However, existing patch pumps still present a number of drawbacks and their overall adoption is low compared to the use of syringes and syringe pens. Such pumps are rigid and bulky and consequently are prone to detachment and/or require the use of aggressive adhesives to adhere to the skin, which can lead to irritation. Further, because existing pumps usually contain a single reservoir or at most two (e.g. reservoirs for insulin and potentially glucagon), they are also limited in their ability to deliver combination therapies, requiring patients to use separate patch pumps to deliver multiple medicaments. In addition, the use of a single or dual reservoir(s) can make it difficult to control the delivery of accurate amounts of medicament. Some prior art pumps require a flow meter to determine the amount of medicament delivered, which can lead to imprecise measurements.

Accordingly, there exists a need for an improved patch pump.

SUMMARY OF THE INVENTION

A bandage-like patch pump for actively controllable subcutaneous delivery of one or more medications, operating by means of a flexible pump mechanism, includes valves and micro Channels embedded in a flexible substrate, and multiple rigid drug reservoirs that deliver precise volumes of liquid set in motion by the pressure change created by a membrane undergoing unfolding, stretching or another transformation. The mechanism driving the membrane's transformation can be electrolysis, thermal bubble, thermal expansion of wax (or other temperature sensitive material), or a phase change/same phase expanding and/or shrinking, which causes a volume change. The thin, flexible bandage-like form factor enabled by the invention allows for a more comfortable device that can fit the curvature of the human body and be hidden beneath a patient's clothes to protect privacy. The device requires less aggressive adhesive, is less prone to detachment, and is more comfortable and less irritating to the skin than existing devices, while not compromising its delivery or absorption accuracy. The pump includes the potential to deliver multiple medications simultaneously and/or sequentially in one device. Embodiments of the invention use an array of multiple tiny rigid reservoirs, rather than a single large reservoir, which allows for the accurate and safe delivery of precise amounts of one or more medicaments. With the reservoirs embedded in a flexible substrate, even though each reservoir is rigid, the flexible space between reservoirs enables the device to maintain an overall form factor which is highly flexible.

In general, in one aspect, embodiments of the invention feature a patch pump for delivering a medicament to a patient. The patch pump includes a flexible layered structure that includes: a reservoir layer including rigid reservoirs adapted to contain medicament disposed in a flexible material; a flexible microfluidic layer including an element for sealing the rigid reservoirs, a network of microfluidic channels connecting the rigid reservoirs, and at least one outlet valve connected to the network; and a flexible-rigid electronic circuit layer below the microfluidic layer including individually-addressable actuators.

In various embodiments, the rigid reservoirs can be arranged in an array. In some embodiments, at least a portion of an interior surface of each rigid reservoir forms at least one channel. The pump can include at least three rigid reservoirs. The rigid reservoirs can include at least one of glass, polymer, and polypropylene and the flexible material can include at least one of elastomer, protein hydrogel, polyurahane, and polyethylene. Each rigid reservoir may be adapted to contain a volume of medicament in a range from about 10 nanoliters to about 10,000 microliters, and in some instances in a range from about 6 microliters to about 135 microliters. The sealing material can be a compliant membrane that can include at least one of a resilient material and a folded material, and in some cases can include polyethylene. In some embodiments, the flexible microfluidic layer has a laminated structure that includes an upper layer adhered to a middle layer adhered to a lower layer, which can form inlet and outlet valve pairs corresponding to the rigid reservoirs, Each valve may be a one-way valve. The inlet and outlet valve pairs may be formed from corresponding apertures and resilient blocking portions. In some embodiments, the middle layer may not be adhered at each valve, allowing pressurized fluid to flow through each valve. In certain embodiments, the network of microfluidic channels includes an inner tubing encapsulated by a flexible packaging. The inner tubing and flexible packaging may include different materials, for example, the inner tubing may include polyethylene and the flexible packaging may include polyurethane. In some embodiments, each actuator is adapted to contain at least one of an electrolytic material, a volume change material, and a shape change material. The actuators may operate based on one or more of the following techniques: electrolysis of liquid, electrolysis of hydrogel, a piezoelectric technique, a thermopneurnatic technique, an electrostatic technique, a pneumatic technique, a linear piston drive mechanism, a rotary drive mechanism, a shape change mechanism, a phase change technique, an electrowetting/thermocapillary technique, an electrohydrodynamic technique, an electroosmotic technique, a magnetohydrodynamic technique, an electrochemical technique, and a selectively permeable membrane technique. The flexible-rigid electronic circuit layer may be made of stretchable electronics and/or rigid-flexible circuitry, and may be adapted to permit filling of each actuator. In some embodiments, the individually-addressable actuators may include individually-addressable electrode pairs, which may be made of stainless steel, iron, nickel, cobalt, Fe—Ni alloy, indium tin oxide, gold, platinum, a coating film comprising a low surface energy material, fluorine, and alloys and combinations thereof. In some instances the individually-addressable electrode pairs may include a working perimeter electrode surrounding a counter electrode. In some instances, the individually-addressable electrode pairs may be adapted to contact an electrolyte (e.g., an aqueous ion solution). In some embodiments the pump can have a thickness of up to about 5 millimeters. The pump may further include at least one inlet and/or an outlet in fluidic communication with the reservoir layer. The pump may further include a controller connected to the flexible electronic circuit layer, where the controller is adapted to selectively energize the actuators. The pump may further include a power source for powering the controller and/or the actuators.

In general, in another aspect, embodiments of the invention feature a method of using a flexible patch pump. The method may include the steps of providing a flexible patch pump including rigid reservoirs disposed in a flexible material and corresponding actuators, adhering the flexible patch pump to a skin surface of a patient, and controlling the flexible patch pump to selectively energize at least one of the actuators to deliver medicament disposed in the corresponding rigid reservoir to the patient.

In various embodiments, the method can further include the step of filling the rigid reservoirs with medicament. The method can further include the step of subcutaneously inserting a cannula fluidicly connecting the flexible patch pump with the patient. The method can further include the step of removing the flexible patch pump from the skin surface.

In general, in another aspect, embodiments of the invention feature a method of manufacturing a flexible patch pump. The method may include the steps of providing a reservoir layer including a plurality of rigid reservoirs adapted to contain medicament disposed in a flexible material; adhering to the reservoir layer a flexible microfluidic layer including an element for sealing the rigid reservoirs, a network of microfluidic channels connecting the rigid reservoirs, and at least one outlet valve in the network; and adhering below the flexible microfluidic layer a flexible-rigid electronic circuit layer including individually-addressable actuators.

In various embodiments, the method can further include the steps of adhering below the flexible-rigid electronic circuit layer at least one of a pressure sensitive adhesive layer and a hydrogel layer, filling the rigid reservoirs with medicament, and/or disposing in the actuators at least one of an electrolytic material, a volume change material, and a shape change material. The method can further include the steps of sterilizing a least a portion of the flexible patch pump, connecting a controller to the flexible-rigid electronic circuit layer, connecting a power source to the flexible patch pump, connecting an infusion set to an outlet of the flexible patch pump, and/or verifying operation of the flexible patch pump. In some embodiments, the network of microfluidic channels includes a plurality of materials, which in some cases can include polyethylene channels formed by supersonic or ultrasonic welding encapsulated in another material.

BRIEF DESCRIPTION OF THE FIGURES

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings.

DESCRIPTION

Embodiments of the present invention are directed to a patch pump having a flexible layered laminated structure. This structure results in a pump that is less prone to detachment, more comfortable, and less irritating to the skin than existing pumps with hard, inflexible housings, while meeting or improving delivery accuracy of alternative pumps. In some embodiments, the patch pump of the present invention can be significantly thinner than existing pumps, in some cases having a thickness less than or equal to about 5 millimeters, which allows the pump to be concealed comfortably beneath a patient's clothing. Further the pumps according to the invention can allow for the delivery of multiple medicaments using a single device. In a particular embodiment, layered laminated structure may include a reservoir layer including a plurality of rigid reservoirs disposed in a flexible material, a flexible microfluidic layer including a compliant membrane that seals the rigid reservoirs, and a flexible-rigid electronic circuit layer below the microfluidic layer having a plurality of individually-addressable actuators. The configuration and operation of each of these layers are discussed in greater detail below.

Figure 1:
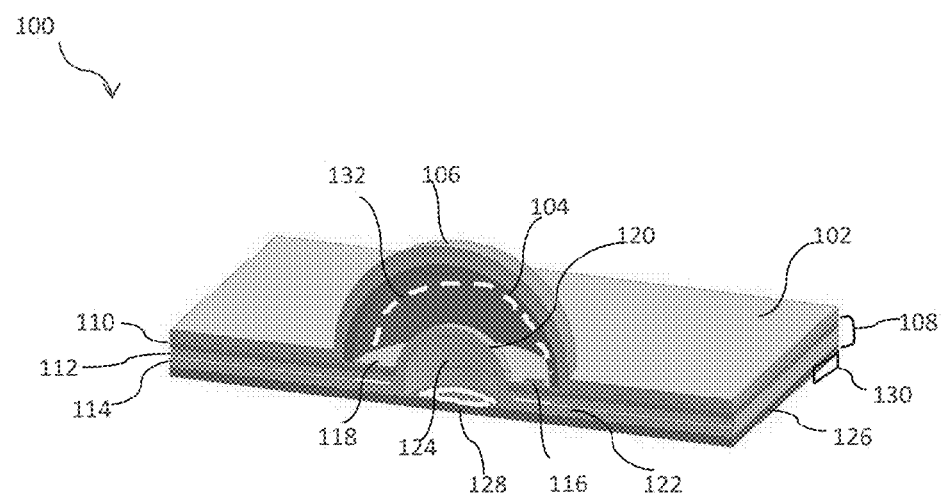
FIG. 1 is a schematic, perspective cross-sectional enlarged view of a portion of a patch pump according to one embodiment.
Figure 2:
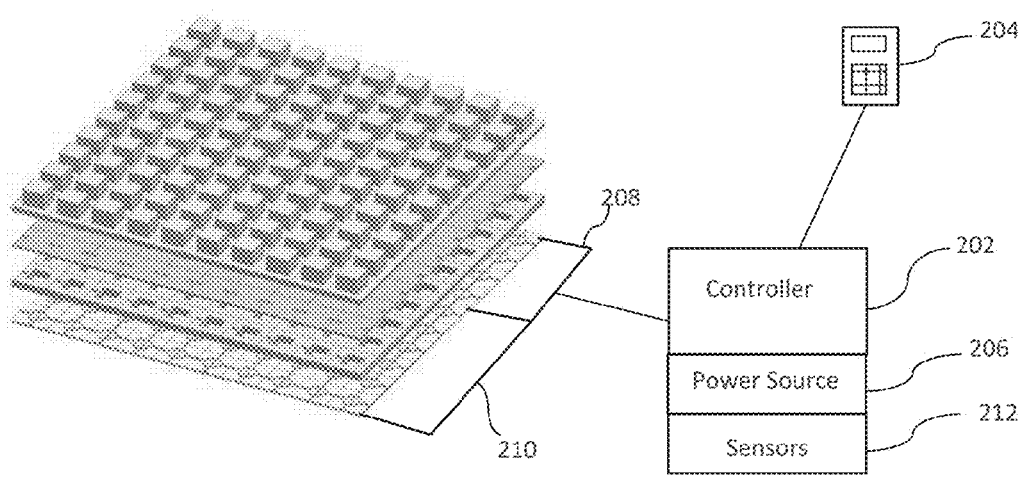
FIG. 2 is a schematic, perspective exploded view of the patch pump according to one embodiment.

FIG. 1 shows a schematic section view of a portion of a patch pump 100 of an embodiment of the present invention. In various embodiments the pump 100 includes a reservoir layer 102 having a plurality of rigid reservoirs 104 disposed in a flexible material 106. Although FIG. 1 only depicts a single rigid reservoir 104, the pump 100 typically contains a plurality of rigid reservoirs (e.g., 10, 50, 100, 1000 or more) which, in some instances, are arranged in an array as shown in FIG. 2. Further, although the rigid reservoir 104 is depicted in a hemispherical shape in FIG. 1, the rigid reservoirs can be formed in any shape, for example, a rectangular prism or cube shape as shown in FIG. 2. The rigid reservoirs 104 may be manufactured from hard plastics (e.g., polymers), resin, glass, and/or polypropylene or other material. Such materials provide the reservoirs with a rigid structure capable of containing medicament (e.g., insulin) and prevent the volume of each reservoir from being altered, which prevents medicament from being inadvertently released upon external impact (e.g., if the patch pump is stretched, bent, or squeezed). The flexible material 106 within which the rigid reservoirs are disposed, holds the rigid reservoirs 104 together and ensures the overall flexibility of the pump 100. The flexible material 106 can include an elastomer, elastic resin, protein hydrogel, polyurethane, and/or polyethylene or other material. Use of a plurality of rigid reservoirs allows the volume of medicament contained in each individual reservoir to be significantly lower than in other devices (e.g., single or dual reservoir pumps). This can increase safety, by lowering the volume which might be errantly released from a reservoir of the pump, providing better control and accuracy of the device. In some embodiments, each rigid reservoir is adapted to contain a volume of medicament in a range from about 10 nanoliters to about 10,000 microliters. A typical reservoir volume for insulin may be in a range from about 6 microliters to about 135 microliters, and in some cases in a range from about 10 microliters to about 100 microliters. The reservoirs 104 may all contain the same volume or differing volumes, as desired for a particular application.

In various embodiments, the pump 100 includes a flexible microfluidic layer 108. The flexible microfluidic layer 108 may include an element, such as compliant membrane 120 for sealing the rigid reservoirs, an example of which is shown in FIG. 1. The compliant membrane 120 may be a resilient and/or folded material, which is actuated to reduce the volume and thereby increase the pressure within each rigid reservoir, evacuating at least some of the medicament contained therein. The compliant membrane may be polyethylene or other material suitable for the medicament to be pumped. In various embodiments, the compliant membrane 120 or other force or pressure transmitting element (or structure to be displaced into the reservoir volume) can be actuated using at least one of the following techniques: electrolysis of liquid, electrolysis of hydrogel, thermal expansion of wax, a piezoelectric technique, a thermopneumatic technique, an electrostatic technique, a pneumatic technique, a linear piston drive mechanism, a rotary drive mechanism, a phase change technique, an electrowetting/thermocapillary technique, an electrohydrodynamic technique, an electroosmotic technique, a magnetohydrodynamic technique, an electrochemical technique, and an ion-permeable membrane technique. In embodiments in which the compliant membrane 120 is actuated using a fluid (e.g., electrolysis of a fluid), the flexible microfluidic layer 108 may at least partially define a chamber 124 for containing an actuating fluid. In some instances, the actuating fluid may be an electrolytic material. For example, the electrolytic material may be any aqueous solution containing ferrous ions or other metal ions in which the metal has a negative standard potential in an aqueous solution with reference to a normal hydrogen electrode. In other instances, the actuating fluid may be a volume change material, for example, piezoelectric zirconate titante, heat actuated phase change materials (e.g., paraffin), shape memory materials (e.g., Ni—Ti), and shape change polymers (e.g., Ni—Zn containing polymers) A more detailed discussion of actuating the compliant membrane 120 is presented below in conjunction with description of the flexible-rigid electronic circuit layer and a method of using the patch pump 100. Although FIG. 1 only shows a single compliant membrane 120, the flexible microfluidic layer 108 may include a continuous membrane for the entire pump 100, or a discrete compliant membrane 120 corresponding to each rigid reservoir 104 or separate membranes each corresponding to a subset of rigid reservoirs 104.

Figure 3:
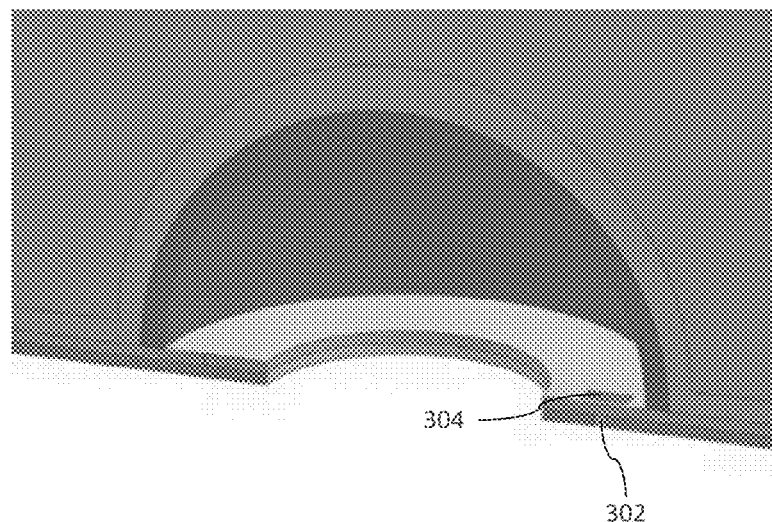
FIG. 3 is a schematic, perspective cross-section view of a valve including an aperture and a corresponding resilient blocking portion.
Figure 4:
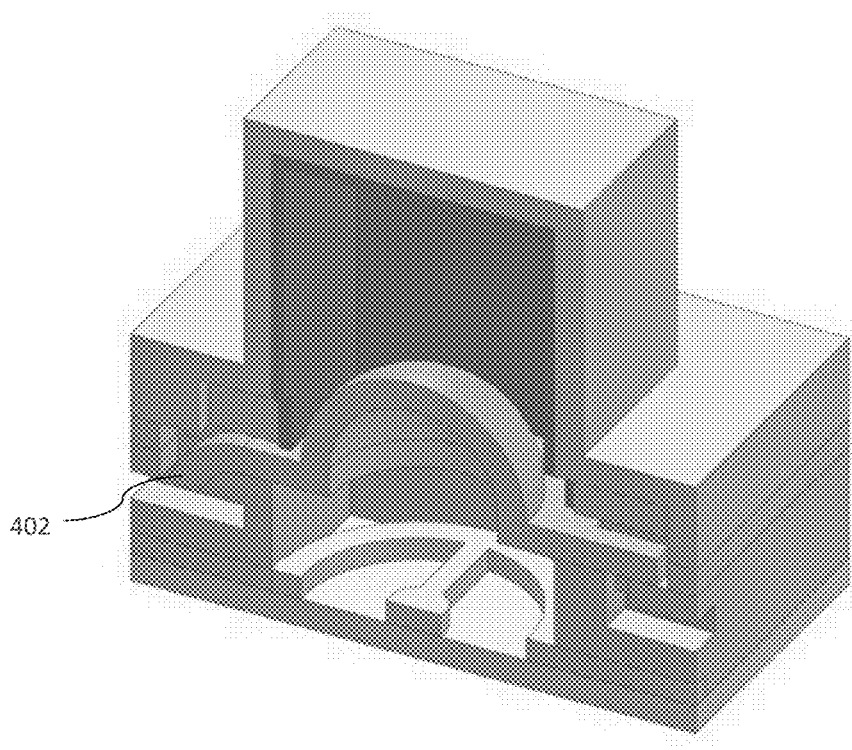
FIG. 4 is a schematic, perspective cross-section view of a flap valve.

In various embodiments the flexible microfluidic layer 108 may include valves through which medicament can be transported into and out of the rigid reservoirs 104. In some instances, an upper layer 110 of the microfluidic layer 108 can be selectively adhered to a middle layer 112 to form a plurality of inlet valves 116 and/or a plurality of outlet valves 118, both of which can be one-way valves. Although FIG. 1 only shows a single inlet valve 116 and a single outlet valve 118, the flexible microfluidic layer 108 may include an inlet and/or outlet valve corresponding to each rigid reservoir 104, as shown for example in FIG. 2. In some embodiments each valve is formed by an aperture 302 that corresponds with a resilient blocking portion 304, as shown for example in FIG. 3. In such embodiments, the middle layer 112 may not be adhered to the upper layer 110 at the location of each valve, allowing deflection in the valve stack to permit fluid to flow through each valve. In other embodiments, the valves are flap valves 402 as shown, for example, in FIG. 4 that include a cantilever beam element biased in a normally closed configuration and that bends or deflects when subject to a pressure differential to permit flow in a single direction only. Other valve configurations are also possible. In other instances, the valves can be formed in a single layer of material. Further, although FIG. 1 depicts the compliant membrane 120 as part of a lower layer 114 adhered below the upper layer 110 and middle layer 112 that form the valves, in some embodiments the compliant membrane 120 can be disposed within or as part of the layer(s) forming the valves, as shown for example in FIG. 4.

In various embodiments, the flexible microfluidic layer 108 can include at least one microfluidic channel 122 for fluidicly communicating an outlet valve of each reservoir with an outlet 502 of the pump. Although FIG. 1 depicts the microfluidic channels 122 as part of the lower layer 114 adhered below the upper layer 110 and middle layer 112 forming the valves, in some embodiments the microfluidic channels 122 can be formed in the same layer(s) that form the valves.

Figure 5A:
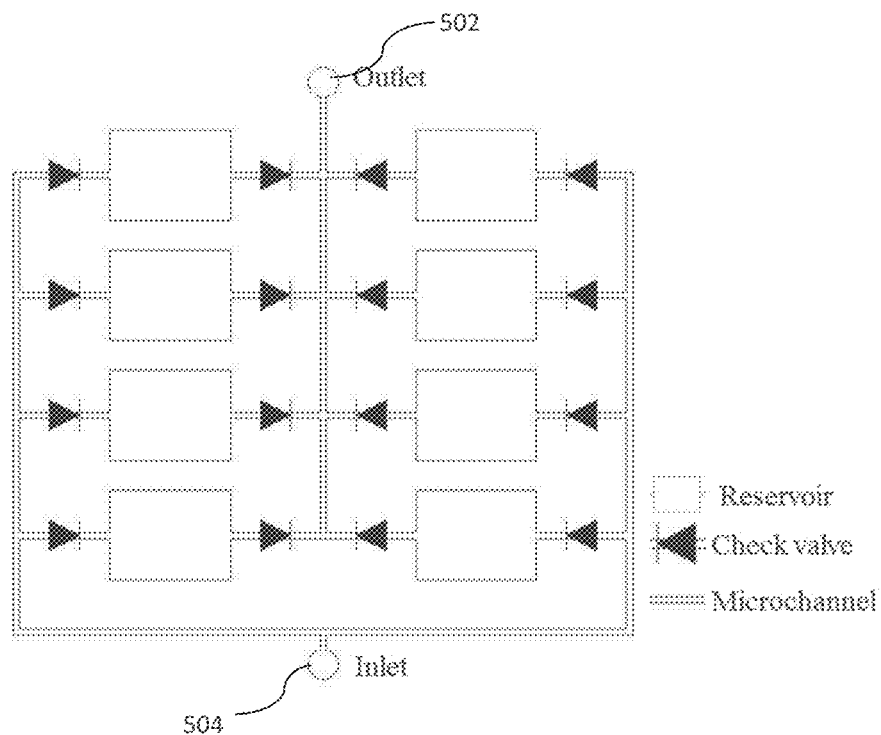
FIG. 5A is a schematic fluidic diagram showing an embodiment of the invention having a single pump inlet and a single pump outlet.
Figure 5B:
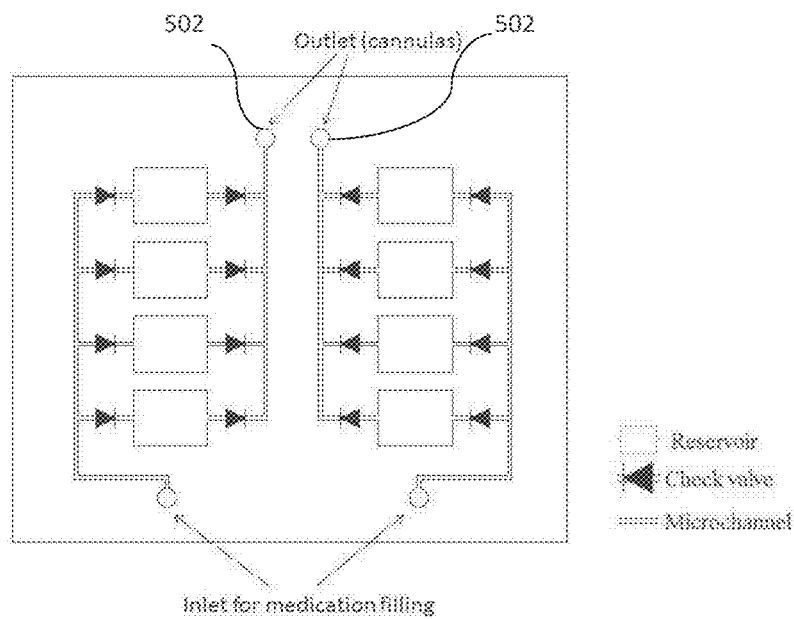
FIG. 5B is a schematic fluidic diagram showing an embodiment of the invention having multiple pump inlets and multiple pump outlets.

The microfluidic channels 122 can all be similarly sized or they can be of different sizes, for example with a plurality of small channels connecting each reservoir 104 to a larger trunk or main channel directly connected to the outlet 502. The microfluidic network of channels 122 can connect to the outlet 502 of the pump, as shown in FIG. 5A. In some embodiments, the pump may include multiple outlets, as shown in FIG. 5B. An embodiment including multiple outlets may be used, for example, to deliver different types of medicament (e.g., different types of insulin and/or glucagon to provide an artificial pancreas function) or to deliver different dose amounts of medicament e.g., one outlet for a basal dose and another outlet for a bolus dose). Such an embodiment with two or more fluidic networks may be used to deliver different fluids, flow rate amounts, etc., and/or to prevent cross-contamination. Each outlet 502 can be adapted to deliver medicament to an infusion set, which in some cases can include a subcutaneous cannula, to provide a fluidic pathway from the pump 100 to the patient. Some embodiments of the pump 100 are adapted to interface with commercially available infusion sets, for example by using a flexible tube to connect the outlet 502 to the infusion set.

In various embodiments, the pump 100 includes a flexible-rigid electronic circuit layer 126 below the microfluidic layer 108. The electronic circuit layer 126 can include stretchable electronics or in some cases, rigid-flexible circuitry, Stretchable electronics are electronics that are stretchable, bendable, and compressible. The electronic circuit layer 126 may include a plurality of individually-addressable actuators 128 and/or subsets of simultaneously addressable actuators (e.g., to deliver a bolus dose). Although FIG. 1 only depicts a single actuator 128, the electronic circuit layer 126 may contain a plurality of actuators each corresponding to a single rigid reservoir 104 (as shown in FIG. 2) or multiple rigid reservoirs 104. In general, an actuator can be any device adapted to facilitate actuating the compliant membrane 120 or otherwise applying a force or pressure to discharge at least some of the fluid in the reservoir using one of the following techniques: electrolysis of liquid, electrolysis of hydrogel, thermal expansion of wax, a piezoelectric technique, a thermopneumatic technique, an electrostatic technique, a pneumatic technique, a linear piston drive mechanism, a rotary drive mechanism, a phase change technique, an electrowetting/ thermocapillary technique, an electrohydrodynamic technique, an electroosmotic technique, a magnetohydrodynamic technique, an electrochemical technique, and an ion-permeable membrane technique. Each rigid reservoir 104 may include a flow channel 132 on its interior surface that provides a fluidic pathway for medicament to exit the reservoir 104 even in instances Where compliant membrane 120, in its expanded state, blocks outlet valve 118. In some cases, compliant membrane 120 may be designed/configured such that even in its expanded state it does not block medicament from exiting the reservoir 104 through outlet valve 118.

In embodiments in which the compliant membrane 120 is actuated using an electrolysis technique, each actuator 128 can include an individually-addressable electrode pair, which can be adapted to apply a voltage differential to an electrolytic fluid. The electrodes may be any suitable material, such as stainless steel, iron, nickel, cobalt, Fe—Ni alloy, indium tin oxide, gold, platinum, and alloys and combinations thereof. In some embodiments, the flexible-rigid electronic circuit layer 126 may be adapted to permit filling of the electrolytic fluid into the chamber 124, for example via at least one hole that can be sealed after filling.

Figure 6:
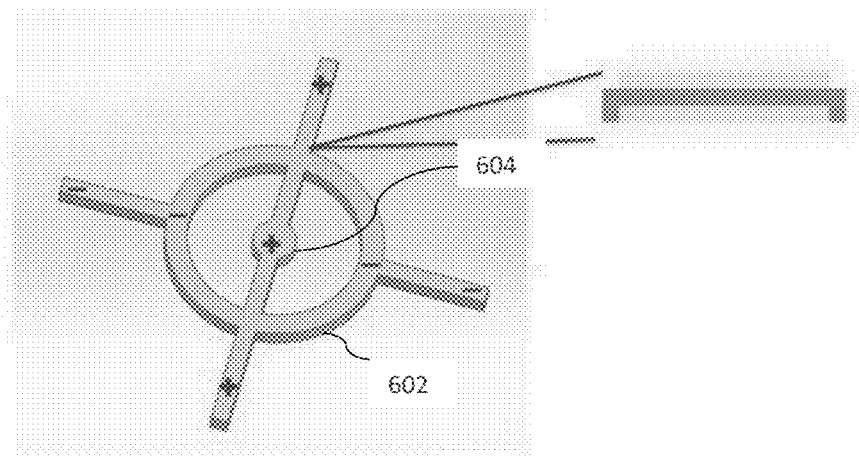
FIG. 6 is a schematic, perspective view of an embodiment of an electrode pair.

The electrode pairs may be a working perimeter electrode 602 surrounding a counter electrode 604, as shown for example in FIG. 6. The plus sign denotes the positive cathode and the minus sign denotes the negative anode. In such instances, one of the electrodes can stimulate formation of a gas (e.g. hydrogen). While the other electrode contacts an electrolyte (e.g. an aqueous solution or potassium chloride). Although FIG. 6 appears to be one continuous structure, in actuality the cathode electrode is electrically isolated from the anode electrode by insulators at the contact points. For example, after a first layer of gold or other conductive material is deposited using a mask, an insulating material is deposited at the contact points where, otherwise, the cathode and anode would touch. Thereafter, the second layer of gold or other conductive material is deposited using a different mask, to produce each electrically isolated electrode pair.

In various embodiments the pump 100 includes a controller 202 (FIG. 2) to control addressing the actuators. The controller may include a transceiver (e.g., a blue-tooth transceiver), a microprocessor, a voltage/current regulator, a sensor module (e.g., a module consisting of pressure and temperature sensors), an analog switch, and a reporter. The controller can receive instructions wirelessly from a remote control unit 204 (e.g., a handheld device, smartphone, or smartphone-like device) operated by the patient. In one embodiment, the pump system includes a transceiver 208, a patch pump, and an infusion set 210. The transceiver 208 communicates with the remote control unit 204, sending out patch pump status to and receiving instructions from the remote control unit 204. Upon receiving instructions from the remote control unit 204, the transceiver 208 adjusts the volume and/or rate of drug delivery from the patch pump. The patch pump is electrically connected to the transceiver 208, stores the drug to be delivered, and delivers the drug to subcutaneous tissue through the infusion set 210. The infusion set 210 is connected to the outlet of the patch pump. Communication between the remote control unit 204 and the pump may occur wirelessly over Bluetooth, or the internet. The pump 100 also includes a power source 206 for powering the controller and the actuators.

As mentioned above, it is important that a medicament pump be able to deliver precise amounts of medicament accurately. One challenge to delivering medicament accurately over extended periods is that various parameters affecting medicament flow rate can change over time. In certain embodiments, the pump may include operational and/or environmental sensors 212 (FIG. 2) for sensing flow rate as well as conditions that may affect flow rate and/or operation of the pump, for example, ambient air temperature and pressure, current flow, voltage, external forces, and wireless connectivity. The sensor readings can be communicated to the controller, which can automatically adjust the pump's operation e.g., its volume and rate of delivery), if sensed readings exceed or fall below a desired range. In some instances, the device adjusts the pump's operation each time the pump delivers a predetermined amount of medicament. In other instances, the device adjusts the pump's operation at predetermined time intervals. In other embodiments, the pump 100 may include an alarm, display, tactile device, or other notification mechanism that can be triggered if readings extend above or below a desired range or if other alarm conditions exist.

In various embodiments the pump 100 may also include external pressure sensor(s) 130 that can determine whether delivered medicament has been absorbed by the subcutaneous tissue of a patient. Because of the variable resistance to injection inherent in various human tissues, delivered medicament will often diffuse into the subcutaneous fat layer at a slow rate. External pressure sensors 130 can be located against a patient's skin such that they experience a sudden pressure increase following delivery of a medicament (due to an increased area of skin pressing against the sensor), and then a slow pressure drop as the medicament is absorbed into the subcutaneous tissue. When the pressure reading returns to zero, a signal can be generated indicating that all medicament has been absorbed, which in some cases can allow for an additional delivery of medicament to occur.

In another aspect, the present invention relates to a method of using the flexible patch pump. The method can include adhering the patch pump to a skin surface of a patient. A patient controls the pump to deliver medicament disposed therein, for example by selectively addressing at least one of the actuators. Addressing a particular actuator associated with a particular rigid reservoir causes the compliant membrane or other element corresponding to that rigid reservoir to expand into and increase the pressure within the rigid reservoir or otherwise displace the contents of the rigid reservoir. Under the increased pressure, medicament may be evacuated from the rigid reservoir through an outlet valve, into a microfluidic channel from which it can be delivered to the pump outlet and ultimately an infusion set for subcutaneous delivery into the patient. The outlet valves in the microfluidic network prevent back-flow of the medicament into the reservoir it came from or a neighboring reservoir once it has been evacuated. In general, addressing a particular actuator can include any of the actuating techniques described above. In the embodiment in which the actuators include individually-addressable electrode pairs, addressing a particular actuator can include delivering current to the electrode pairs, which results in a voltage differential being applied to an electrolysis fluid, generating a gas (e.g., hydrogen). The gas volume causes the compliant membrane to expand or unfold into the rigid reservoir, resulting in the evacuation of medicament. In such an embodiment, the amount of medicament evacuated is determined by the magnitude and duration of the compliant membrane's deflection, which corresponds to the applied voltage and the duration of the delivered current.

The pump 100 can be adapted to deliver medicament from a single rigid reservoir (or a portion thereof) or many rigid reservoirs at a given time, depending on how many actuators are addressed. Thus, the pump 100 can be adapted to deliver both basal and bolus doses of medicament. With an electrolytic-based actuator, the flow rate is controlled by the current supply. As one example, potassium chloride solution can be used as the electrolyte and the progress of water electrolysis (with associated gas bubble generation) can be governed by the current supply. In such embodiments, the volume of gas generated can be linear with respect to the amount of time current is applied. In some embodiments, the pump 100 may be adapted to deliver doses as small as 1 nanoliter.

By way of example, the patch pump 100 may deliver basal doses at a flow rate in a range from between about 10 nanoliters per minute to about 1,000 nanoliters per minute, depending on the amount of current delivered to the actuator or actuators. Because basal dose rates are relatively small, a single reservoir may provide the medicament for multiple doses using intermittent actuation techniques. For example, a current may be applied to a particular actuator for a predetermined amount of time e.g., 2 seconds) until a programmed amount of medicament is released (which can be less than the volume contained within the reservoir), after which the current flow stops and the voltage returns to zero. After a predetermined interval (e.g., 3 minutes) current may again be applied to the same actuator, releasing more medicament from the reservoir. This process repeats until all the medicament in a particular reservoir has been released, after which current can be applied to a different actuator. In some instances, depending on the amount of insulin required by the patient and the size of the reservoir, a particular electrode may be actuated multiple times (e.g., between 3 and 7 times) before releasing all of the medicament contained in the reservoir.

In some embodiments, each individual reservoir may be either completely full or completely evacuated, in which case the delivered dose will be pre-determined by the size of the individual reservoirs, which may vary from one medicament reservoir to another.

In various embodiments, the patch pump 100 may deliver bolus doses at a flow rate of up to about 1 milliliter per minute, depending on the amount of current applied to an actuator or actuators. In some instances, in delivering a bolus injection, current may be applied to a particular actuator for a longer period of time than for a basal dose (e.g., 20 seconds), releasing more medicament In other instances, in delivering a bolus injection, several reservoirs may be actuated, either concurrently or sequentially.

Figure 24:
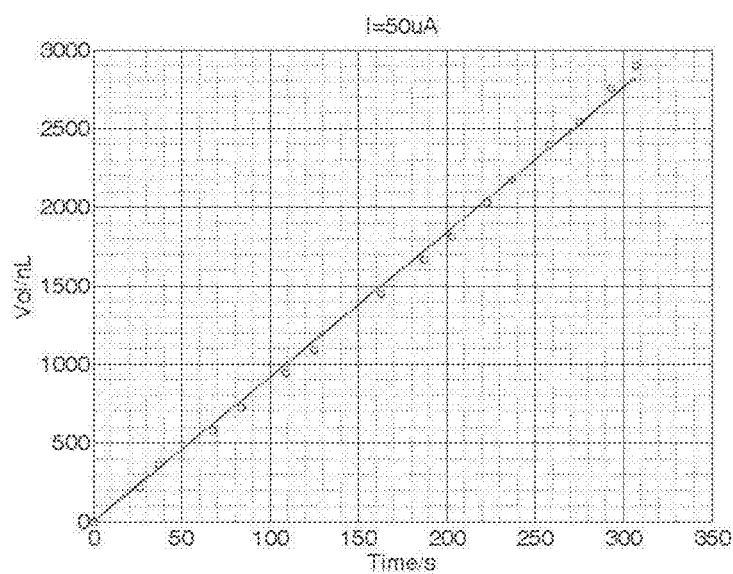
FIG. 24 is a graph showing experimental data of volume of insulin pumped versus time under a constant applied current of 50 microamps.

For example, for a type 1 diabetic patient weighing 70 kilograms, the estimated daily basal insulin injection is 40 units (i.e., 0.4 mL, 1 unit equals 0.01 mL), which is equivalent to 277 nL/min (lower flow rates can be used with ultra-concentrated insulin). Although in some embodiments such a flow rate can be generated through the intermittent actuation techniques described above, in other embodiments this flow rate can be accurately delivered through the constant application of current to the actuators. In an experiment, the data from which is shown in FIG. 24, it has been verified that a constant applied current of 50 microamps creates a linear injection rate of 9.2 nL/s (or 552 nL/min). Depending on the resistance of the electrode material, the applied current may generate a voltage of between 0.5 volts and 5 volts, for example, in one embodiment 0.9 volts.

In embodiments in which different rigid reservoirs contain different medicaments, the pump can be adapted to actuate multiple reservoirs to deliver more than one medicament or a combination of medicaments. In embodiments in which the controller 202 is operated from a remote control unit 204 by a patient, the patient may instruct the controller 202 how much medicament to deliver at a particular trifle e.g., a diabetic may instruct the controller 202 to deliver a bolus dose of insulin prior to a meal) and/or which medicament/combination of medicaments to deliver at a particular time. The controller 202 may then determine which actuators to selectively address in order to deliver the instructed amount of the selected medicament. A combination of medicaments can be blended in the microfluidic network of the pump 100, immediately prior to delivery via a common outlet, if desired.

Figure 7:
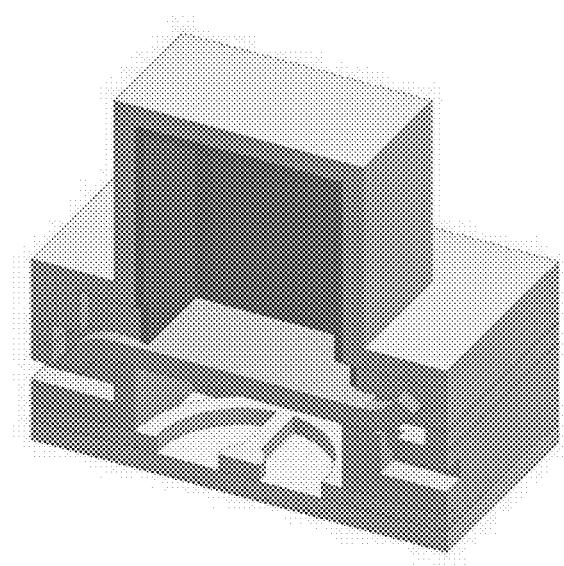
FIG. 7 is a schematic, perspective cross-section view of a portion of the pump showing a configuration of the valves during filling of the pump.

In some embodiments, the rigid reservoirs 104 of the pump 100 may be filled during manufacture of the pump 100. In other embodiments, the pump 100 is fillable after the pump has been manufactured, for example, by the patient. In such embodiments, one method of using the flexible patch pump can further include the step of filling the rigid reservoirs with medicament, by connecting the outlet 502 of the pump to a vacuum, to evacuate any gas contained within the microfluidic channels and reservoirs, while providing a supply of medicament (optionally pressurized) at the inlet 504. The differential pressure opens the inlet and outlet valves associated with each rigid reservoir. An example configuration of the valves during this filling process can be seen in FIG. 7. This process results in all of the rigid reservoirs being filled. Alternatively, the pump can be pre-filled with a sterile saline solution and filled by the user with medicament as described above, immediately prior to use.

Figure 8:
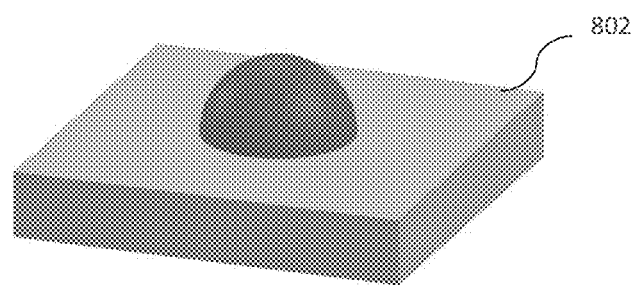
FIG. 8 is a schematic, perspective view of a rigid reservoir being molded on a reservoir mold.
Figure 9:
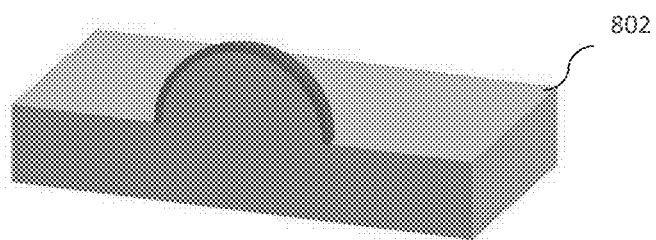
FIG. 9 is a schematic, perspective cross-section view of a rigid reservoir being molded on a reservoir mold.
Figure 10:
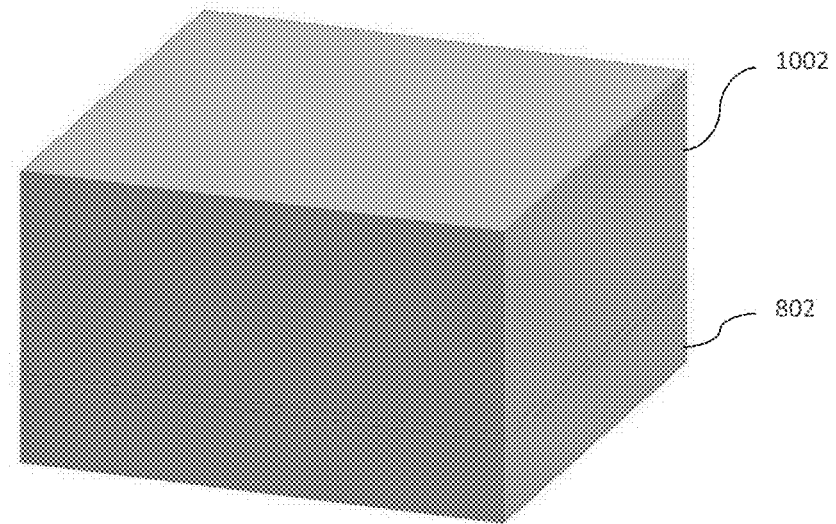
FIG. 10 is a schematic, perspective view of a flexible layer being molded between a reservoir mold and a flexible layer mold.
Figure 11:
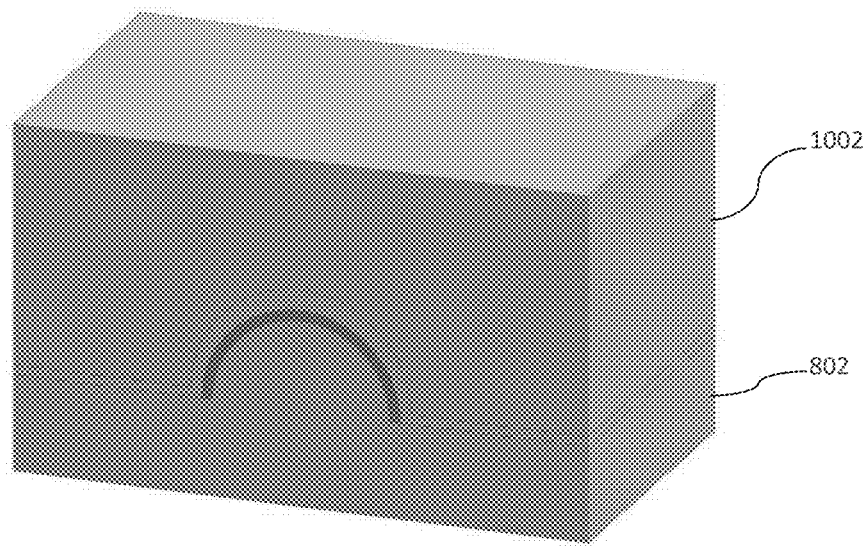
FIG. 11 is a schematic, perspective cross-section view of a flexible layer being molded between a reservoir mold and a flexible layer mold.
Figure 12:
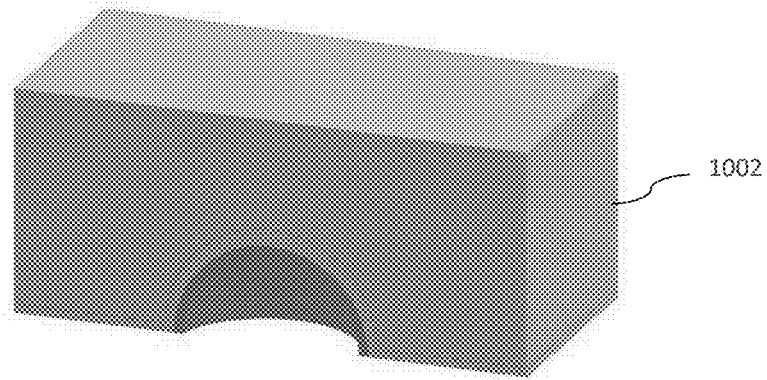
FIG. 12 is a schematic, perspective cross-section view of a flexible layer molded to a rigid reservoir.

Additional aspects of the present invention relate to methods of manufacturing the flexible patch pump. The reservoir layer can be manufactured by molding the rigid reservoirs in a reservoir mold 802, as shown for example in FIG. 8 and FIG. 9, Without peeling the rigid reservoirs from the reservoir mold, the reservoir mold can be positioned close to a flexible layer mold 1002, and the flexible layer molded in between, as shown for example in FIG. 10 and FIG. 11. The rigid reservoirs may be bonded to the flexible layer by the nature of the materials utilized or optionally using a thin layer of adhesive. The rigid reservoirs may then be removed from the reservoir mold 802, as shown for example in FIG. 12. In some instances, the flexible layer mold 1002 can remain attached at this point for easy handling of the reservoir layer during further manufacturing steps.

Figure 13:
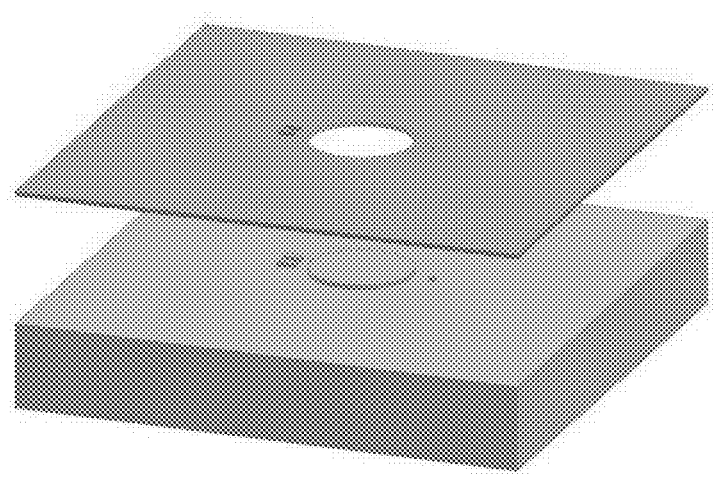
FIG. 13 is a schematic, perspective exploded view of a portion of a valve layer being molded.
Figure 14:
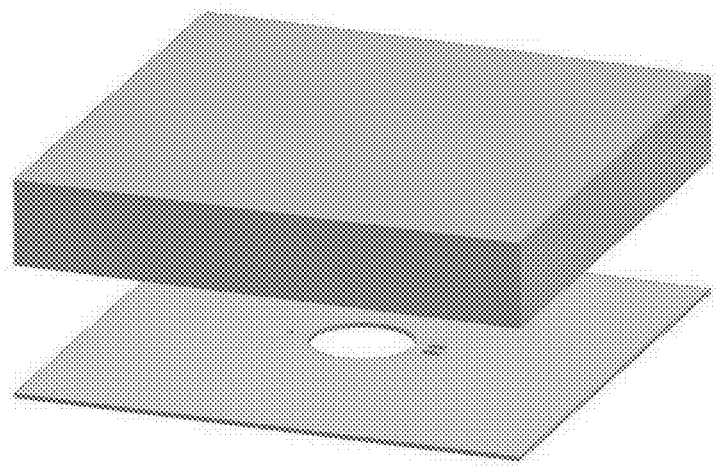
FIG. 14 is a schematic, perspective exploded view of another portion of a valve layer being molded.
Figure 15:
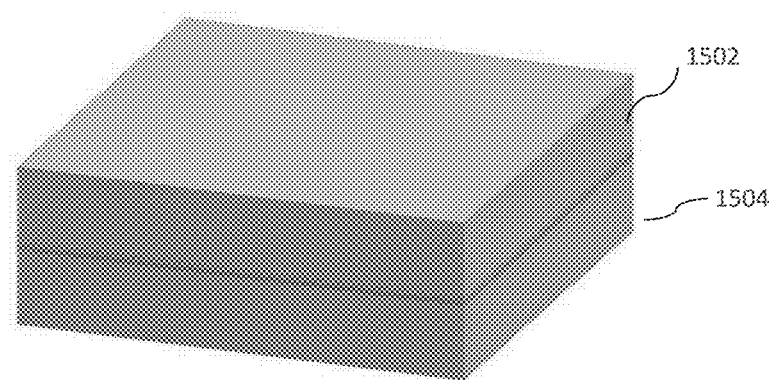
FIG. 15 is a schematic, perspective view of multiple valve layers being molded together.
Figure 16:
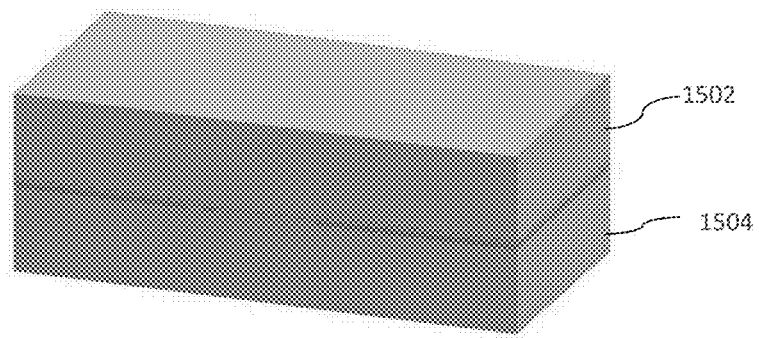
FIG. 16 is a schematic, perspective cross-section view of multiple valve layers being molded together.
Figure 17:
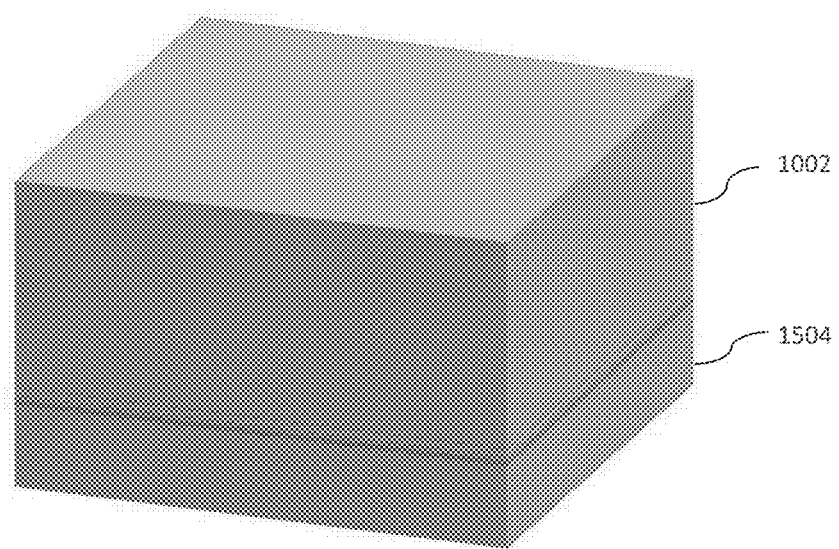
FIG. 17 is a schematic, perspective view of layers forming valves being bonded to a reservoir layer.
Figure 18:
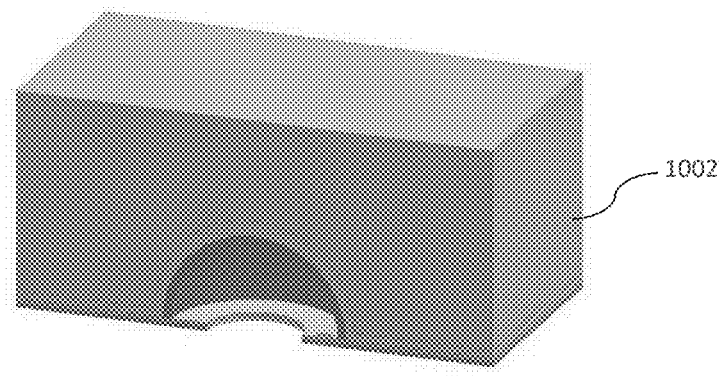
FIG. 18 is a schematic, perspective cross-section view of layers forming valves being bonded to a reservoir layer, with a mid for forming one of the layers removed.

The flexible microfluidic layer can include: (i) a plurality of outlet and/or inlet valves, (ii) a compliant membrane for sealing the rigid reservoirs, and (iii) a network of microfluidic channels connecting the rigid reservoirs. In certain embodiments, fabricating the plurality of outlet and/or inlet valves includes separately molding an upper layer and a middle layer, as shown for example in FIG. 13 and FIG. 14. The upper and middle layers can then be bonded to one another with a thin layer of adhesive, as shown for example in FIG. 15 and FIG. 16. The upper and middle layers may include corresponding structured features that form the valves. For example, each layer may include an aperture that corresponds to a resilient blocking portion of the other layer, and a resilient blocking portion that corresponds to an aperture of the other layer. In certain embodiments, the middle layer may not be adhered to the upper layer at the location of each valve by selectively deactivating the upper and/or middle layers at these locations, Deactivation may be accomplished by removing or not applying adhesive at the location of each valve. In other instances, deactivation may be accomplished by depositing a layer of removable resist (e.g., PMMA) at the location of each valve, and after the upper and middle layer are bonded together, removing the resist using a corresponding solvent (e.g., acetone). After the upper and middle layers are bonded, the upper layer mold 1502 may be removed. The middle layer mold 1504 may remain attached at this point for easy handling of the upper and middle layers during further manufacturing steps. At this point, the upper and middle layers may be bonded to the reservoir layer, as shown in FIG. 17. The middle layer mold 1504 can then be removed, as shown in FIG. 18.

Figure 19:
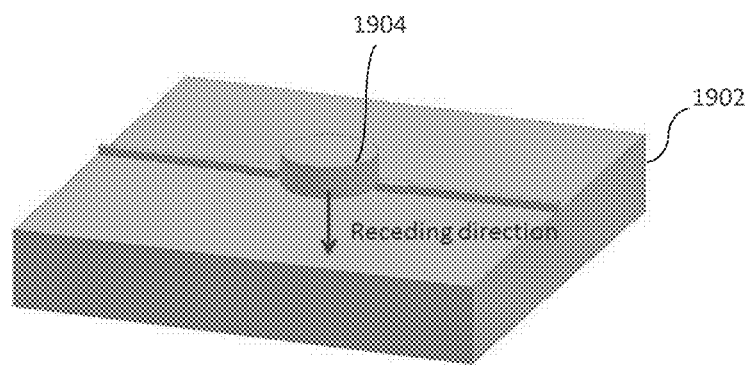
FIG. 19 is a schematic, perspective view of a mold for fabricating a layer including a compliant membrane and microfluidic channels.
Figure 20:
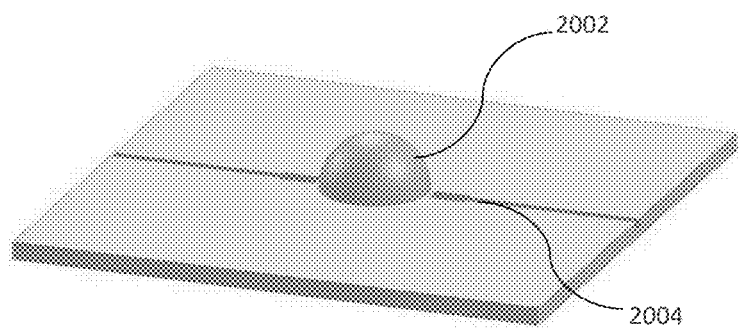
FIG. 20 is a schematic, perspective view of a layer including a compliant membrane and microfluidic channels.

Fabricating the compliant membrane and network of microfluidic channels of the flexible microfluidic layer can include molding a resilient material using the mold 1902 shown in FIG. 19. In embodiments in which the compliant membrane is a folded material, a center piston 1904 can be retracted after molding to create a folded portion. One type of resultant structure is shown in FIG. 20, which includes a compliant membrane 2002 and a microfluidic channel 2004. In other embodiments, the compliant membrane may be fabricated by ion-striking the resilient material.

Figure 21:
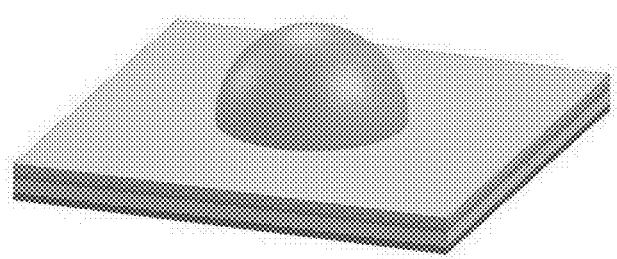
FIG. 21 is a schematic, perspective view of a portion of a fully-assemble patch pump.

The flexible-rigid electronic circuit layer includes a plurality of individually-addressable actuators. This circuit layer can include stretchable electronics and/or rigid-flexible electronics (as described above). The flexible-rigid electronic circuit layer may then be adhered below the layer including the compliant membrane and microfluidic channel(s), which in some cases can forma chamber for containing an actuating fluid. In embodiments in which actuation of the compliant membrane requires a fluid contained in the chamber, the rigid-flexible electronic circuit layer may include at least one hole for filling the chamber. After the chamber is filled, the hole(s) may be sealed. In certain embodiments in which the pump 100 is manufactured with the rigid reservoirs containing medicament, the rigid reservoirs can be filled with medicament prior to being sealed by the compliant membrane. Removal of the flexible layer mold 1002 results in the structure shown, for example, in FIG. 21.

Figure 22A:
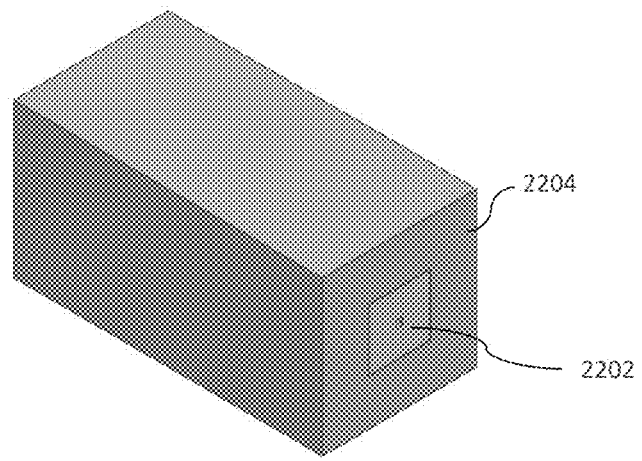
FIG. 22A is a schematic perspective view of a microfluidic channel comprising a plurality of materials according to one embodiment.

In an alternative embodiment, it can be desirable to isolate medicament from the materials in the other layers of the pump, for example by channeling the medicament through a microfluidic network manufactured by a different material. In such embodiments, the microfluidic layer 122 can be made with multiple layers of materials, as shown in FIG. 22A. For example, an inner tubing 2202 of first material can be encapsulated in a flexible packaging material 2204. In some embodiments the inner tubing 2202 can be made of Hi polyethylene and the packaging material 2204 can be made of polyurethane. In such embodiments, the polyethylene tubing is the material in direct contact with medicament, while the polyurethane packaging ensures that structural support and flexibility of the microfluidic layer is maintained.

Figure 22B:
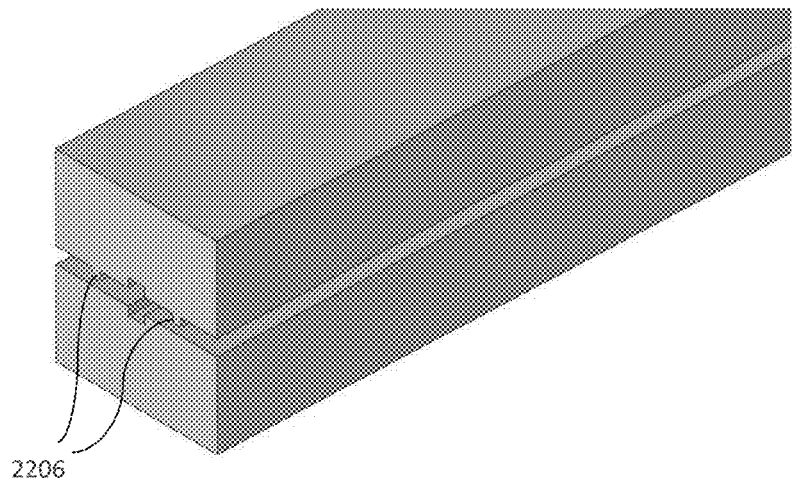
FIG. 22B is a schematic perspective view of a portion of two separate pieces that are ultrasonically welded together to form a microfluidic channel.
Figure 22C:
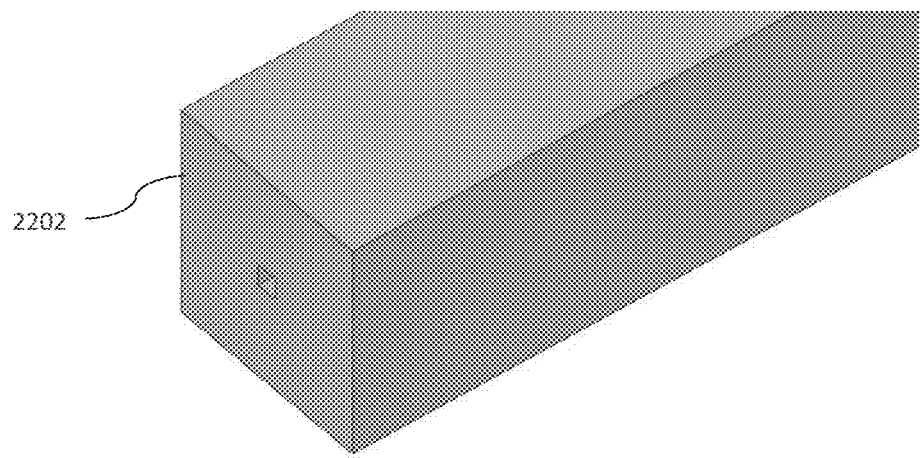
FIG. 22C is a schematic perspective view of a portion of the microfluidic channel of FIG. 22B after ultrasonic welding.

The tubing 2202 can be fabricated using a supersonic or ultrasonic welding process. As shown for example in FIG. 22B, prior to welding, two separate pieces can be molded, at least one having spiked energy directors 2206 (e.g., linear protrusions formed along either side of the flow Channel). During welding, the spiked energy directors 2206 focus the energy and are melted, to join the two pieces to form the tubing 2202, as shown for example in FIG. 22C.

Figure 23A:
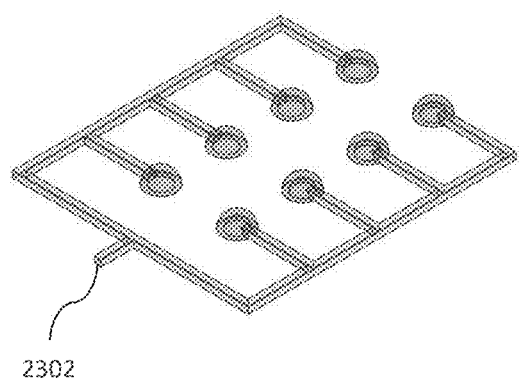
FIG. 23A is a schematic perspective view of a microfluidic channel network in direct fluidic contact with rigid reservoirs according to one embodiment.
Figure 23B:
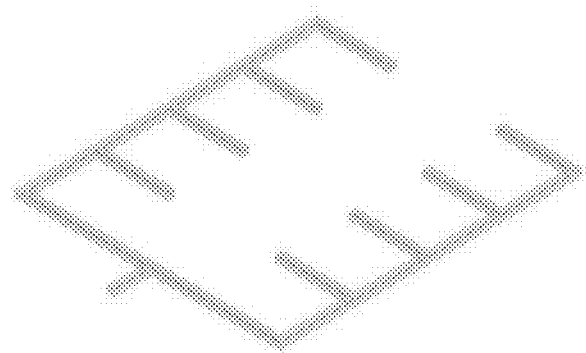
FIG. 23B is a schematic perspective view of a microfluidic channel network according to one embodiment.
Figure 23C:
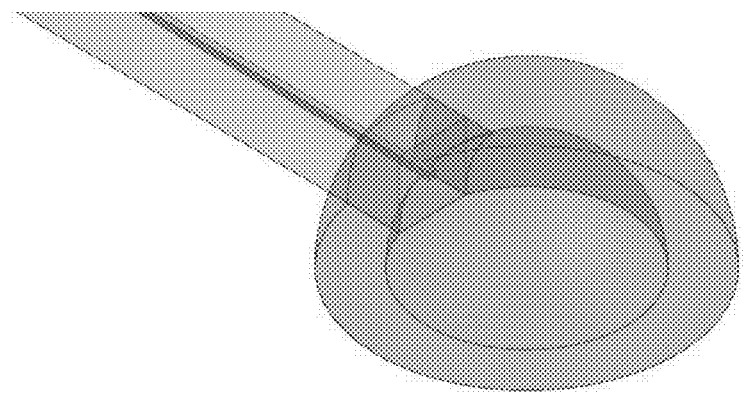
FIG. 23C is a schematic perspective enlarged view of an interface between a microfluidic channel and a rigid reservoir according to one embodiment.
Figure 23D:
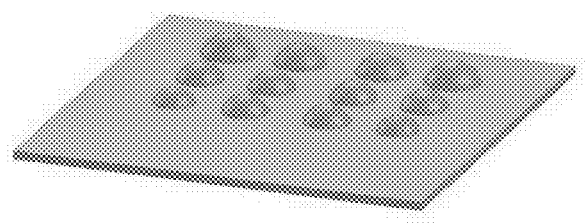
FIG. 23D is a schematic perspective view of a flexible material molded over a microfluidic channel network and rigid reservoirs according to one embodiment.

Alternatively or additionally, rather than being separated from medicament contained within the rigid reservoirs 104 by inlet valves 116 and/or outlet valves 118, the network of microfluidic channels can be in direct fluidic contact with the interior of each rigid reservoir 104, as shown for example in FIG. 23A. Such embodiments may include a common inlet/outlet 2302, which can be connected to one or more valves to control the flow of fluids into and/or out of the pump. Manufacturing such a configuration can include: forming the microfluidic channel network, as shown for example in FIG. 23B, connecting certain channels of the microfluidic channel network to the interior of each rigid reservoir 104, as shown for example in FIG. 23C, and molding a flexible material over the microfluidic channel network and rigid reservoirs, as shown for example in FIG. 23D. In certain embodiments, the microfluidic channels can be made from polyethylene and the rigid reservoirs can be made from polypropylene. The reservoirs may be filled during manufacture or thereafter, for example by at least partially evacuating the pump of gas and permitting the medicament or other fluid to be drawn into the system. Alternatively, the reservoirs can include fill ports that can subsequently be sealed, prior to use of the pump.

Each numerical value presented herein, for example, in a table, a chart, or a graph, is contemplated to represent a minimum value or a maximum value in a range for a corresponding parameter. Accordingly, when added to the claims, the numerical value provides express support for claiming the range, which may lie above or below the numerical value, in accordance with the teachings herein. Absent inclusion in the claims, each numerical value presented herein is not to be considered limiting in any regard.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The structural features and operational functions of the various embodiments may be arranged in various combinations and permutations, and all are considered to be within the scope of the disclosed invention. Accordingly, the described embodiments are to be considered in all respects as only illustrative and not restrictive. Furthermore, the configurations, materials, and dimensions described herein are intended as illustrative and in no way limiting. Similarly, although physical explanations have been provided for explanatory purposes, there is no intent to be bound by any particular theory or mechanism or to limit the claims in accordance therewith.

What is claimed is:

1. A patch pump for delivering a medicament to a patient, the patch pump comprising a flexible layered structure comprising:
    a reservoir layer comprising a plurality of rigid reservoirs disposed in a flexible material and an element for sealing the rigid reservoirs, wherein the rigid reservoirs are adapted to contain medicament;
    a flexible microfluidic layer comprising:
        a network of microfluidic channels connecting the rigid reservoirs; and
        a plurality of outlet valves corresponding to the plurality of rigid reservoirs connected to the network; and
    a flexible-rigid electronic circuit layer below the microfluidic layer comprising a plurality of individually-addressable actuators.

2. The patch pump of claim 1, wherein the plurality of rigid reservoirs are arranged in an array.

3. The patch pump of claim 1, wherein at least a portion of an interior surface of each rigid reservoir forms at least one flow channel.

4. The patch pump of claim 1, wherein the plurality of rigid reservoirs comprises at least three reservoirs.

5. The patch pump of claim 1, wherein the rigid reservoirs comprise at least one of glass, polymer, and polypropylene and the flexible material comprises at least one of elastomer, protein hydrogel, polyurethane, and polyethylene.

6. The patch pump of claim 1, wherein each rigid reservoir is adapted to contain a volume of medicament in a range from about 10 nanoliters to about 10,000 microliters.

7. The patch pump of claim 6, wherein each rigid reservoir is adapted to contain a volume of medicament in a range from about 6 microliters to about 135 microliters.

8. The patch pump of claim 1, wherein the sealing element comprises a compliant membrane comprising at least one of a resilient material and a folded material.

9. The patch pump of claim 8, wherein the compliant membrane comprises polyethylene.

10. The patch pump of claim 1, wherein the flexible microfluidic layer comprises a laminated structure comprising an upper layer adhered to a middle layer adhered to a lower layer.

11. The patch pump of claim 10, wherein the upper, middle, and lower layers form the plurality outlet valves corresponding to the plurality of rigid reservoirs.

12. The patch pump of claim 11, wherein each outlet valve comprises a one-way valve.

13. The patch pump of claim 11, wherein the outlet valves are formed from corresponding apertures and resilient blocking portions.

14. The patch pump of claim 11, wherein the middle layer is not adhered at each outlet valve allowing pressurized fluid to flow through each outlet valve.

15. The patch pump of claim 1, wherein each actuator is adapted to contain at least one of an electrolytic material, a volume change material, and a shape change material.

16. The patch pump of claim 1, wherein each actuator operates based on a technique selected from the group consisting of electrolysis of liquid, electrolysis of hydrogel, a piezoelectric technique, a thermopneumatic technique, an electrostatic technique, a pneumatic technique, a linear piston drive mechanism, a rotary drive mechanism, a shape change mechanism, a phase change technique, an electrowetting/thermocapillary technique, an electrohydrodynamic technique, an electroosmotic technique, a magnetohydrodynamic technique, an electrochemical technique, and a selectively permeable membrane technique.

17. The patch pump of claim 1, wherein the flexible-rigid electronic circuit layer is selected from the group consisting of stretchable electronics and rigid-flexible circuitry.

18. The patch pump of claim 1, wherein the flexible-rigid electronic circuit layer is adapted to permit filling of each actuator.

19. The patch pump of claim 1 wherein the individually-addressable actuators comprise individually-addressable electrode pairs selected from the group consisting of stainless steel, iron, nickel, cobalt, Fe—Ni alloy, indium tin oxide, gold, platinum, a coating film comprising a low surface energy material, fluorine, and alloys and combinations thereof.

20. The patch pump of claim 19, where each individually-addressable electrode pair comprises a working perimeter electrode surrounding a counter electrode.

21. The patch pump of claim 20, wherein each individually-addressable electrode pair is adapted to contact an electrolyte comprising an aqueous ion solution.

22. The patch pump of claim 1, wherein the patch pump comprises a thickness of up to about 5 millimeters.

23. The patch pump of claim 1, further comprising at least one inlet in fluidic communication with the reservoir layer.

24. The patch pump of claim 1, further comprising at least one outlet in fluidic communication with the reservoir layer.

25. The patch pump of claim 1, further comprising a controller connected to the flexible electronic circuit layer, wherein the controller is adapted to selectively energize the actuators.

26. The patch pump of claim 25, further comprising a power source for powering the controller and the actuators.

27. A method of using a disposable flexible patch pump for delivering a medicament to a patient, the method comprising the steps of:
providing a flexible patch pump comprising a plurality of rigid reservoirs disposed in a flexible material connected by a network of microfluidic channels, a plurality of outlet valves corresponding to the plurality of rigid reservoirs, and a plurality of corresponding actuators;
adhering the flexible patch pump to a skin surface of a patient; and
controlling the flexible patch pump to selectively energize at least one of the plurality of actuators to deliver medicament disposed in a corresponding rigid reservoir through a corresponding outlet valve to the patient.

28. The method of claim 27, further comprising the step of filling the rigid reservoirs with medicament.

29. The method of claim 27, further comprising the step of subcutaneously inserting a cannula fluidically connected to the flexible patch pump into the patient.

* * * * *